US008623662B1

(12) United States Patent
Muradov

(10) Patent No.: US 8,623,662 B1
(45) Date of Patent: *Jan. 7, 2014

(54) METHODS OF FORMING VISUAL HYDROGEN DETECTOR WITH VARIABLE REVERSIBILITY

(75) Inventor: Nazim Z. Muradov, Melbourne, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/616,246

(22) Filed: Sep. 14, 2012

Related U.S. Application Data

(62) Division of application No. 13/209,100, filed on Aug. 12, 2011, now Pat. No. 8,268,392, which is a division of application No. 12/038,210, filed on Feb. 27, 2008, now Pat. No. 8,003,055.

(51) Int. Cl.
*G01N 33/00* (2006.01)

(52) U.S. Cl.
USPC ............... 436/144; 436/3; 436/164; 436/166; 422/400; 422/92; 427/212; 427/600; 442/59; 442/63; 442/121

(58) Field of Classification Search
None
See application file for complete search history.

(56) References Cited

U.S. PATENT DOCUMENTS

| 5,849,073 | A | 12/1998 | Sakamoto |
| 6,535,658 | B1 | 3/2003 | Mendoza |
| 6,723,566 | B2 | 4/2004 | Lee |
| 6,895,805 | B2 | 5/2005 | Hoagland |
| 2004/0023595 | A1 | 2/2004 | Ping |
| 2004/0037740 | A1 | 2/2004 | Liu |
| 2004/0115818 | A1 | 6/2004 | Puri |
| 2007/0151850 | A1 | 7/2007 | Wang |
| 2007/0224081 | A1 | 9/2007 | Bokerman |
| 2007/0251822 | A1 | 11/2007 | Hoagland |
| 2008/0233008 | A1 | 9/2008 | Sarkisov |
| 2008/0274344 | A1 | 11/2008 | Vieth |

FOREIGN PATENT DOCUMENTS

JP          2005345338          12/2005

OTHER PUBLICATIONS

Machine translation of JP-2005345338-A Dec. 1, 2005.*
Wittwer, et al., Gasochromic Windows, Solar Energy Materials and Solar Cells, 2004, pp. 305-314, vol. 84.
Smith, et al., Protective Coatings for Pd-Based Hydrogen Sensors, Prepr, Pap. Am. Chem. Soc., Div. Fuel Chem., 2004, pp. 968-969, vol. 49, No. 2.

* cited by examiner

*Primary Examiner* — Sally Merkling
(74) *Attorney, Agent, or Firm* — Brian S. Steinberger; Phyllis K. Wood; Law Offices of Brian S. Steinberger, P.A.

(57) ABSTRACT

Methods, processes and compositions are provided for a visual or chemochromic hydrogen-detector with variable or tunable reversible color change. The working temperature range for the hydrogen detector is from minus 100° C. to plus 500° C. A hydrogen-sensitive pigment, including, but not limited to, oxides, hydroxides and polyoxo-compounds of tungsten, molybdenum, vanadium, chromium and combinations thereof, is combined with nano-sized metal activator particles and preferably, coated on a porous or woven substrate. In the presence of hydrogen, the composition rapidly changes its color from white or light-gray or light-tan to dark gray, navy-blue or black depending on the exposure time and hydrogen concentration in the medium. After hydrogen exposure ceases, the original color of the hydrogen-sensitive pigment is restored, and the visual hydrogen detector can be used repeatedly. By changing the composition of the hydrogen-sensitive pigment, the time required for its complete regeneration is varied from a few seconds to several days.

17 Claims, 7 Drawing Sheets

METHODS OF FORMING VISUAL HYDROGEN DETECTOR WITH VARIABLE REVERSIBILITY

CROSS REFERENCE TO RELATED APPLICATIONS

This is a Divisional of application Ser. No. 13/209,100 filed Aug. 12, 2011, now U.S. Pat. No. 8,268,392, which is a Divisional of application Ser. No. 12/038,210 filed on Feb. 27, 2008, now U.S. Pat. No. 8,003,055. The entire disclosure of each of the applications listed in this paragraph are incorporated herein by specific reference thereto.

STATEMENT REGARDING FEDERALLY SPONSORED RESEARCH

The subject invention was made with government support under NASA, Glenn Research Center, Grant No. NAG3-2751. The government has certain rights in this invention.

FIELD OF INVENTION

The present invention is related to visual hydrogen detecting and, in particular, to methods, processes and compositions for forming, sensing and detecting hydrogen leakage or the presence of hydrogen in a confined environment.

BACKGROUND AND PRIOR ART

With the widespread application of hydrogen as an ecologically clean fuel and a potential substitute for petroleum-based fuels, the safety issues concerning handling of hydrogen on a large scale become a high priority. The ability to monitor hydrogen leakage at production, storage, transmission and usage sites is crucial for its safe handling and use.

The low explosion limits of hydrogen combined with the lack of odor and invisibility of its flame makes the detection of this gas especially difficult and dangerous. Hydrogen has the highest diffusivity of any gas, thus, when it leaks, it can form an explosive mixture with oxygen in the air, which has a lower explosive limit of about 4% $H_2$ in air. The use of odorants for detecting hydrogen leaks by sensing odor, similar to odorizing natural gas by mercaptans, may not be desirable because this could potentially create problems in some hydrogen application areas, such as fuel cells, a liquid hydrogen fuel for Space Shuttle, and the like.

Conventional hydrogen detectors and commercially-available hydrogen sensors fall into five main categories: catalytic combustion, electrochemical, semiconductor-based, thermal conductivity and chemochromic or visual detectors. The existing hydrogen leak detectors and sensors have several drawbacks. First, their use is time consuming and laborious especially when very large areas must be monitored.

Secondly, some of them are not conducive for continuous monitoring, and many exhibit loss of sensitivity in the field due to wind effects, UV radiation from sun, and the like. Many conventional sensors are susceptible to much interference and some of them, for example, catalytic combustion type, are not specific to hydrogen and may produce a false alarm if other combustible gases such as methane, ammonia, carbon monoxide, or propane are present.

Some of the existing formulations involve very active combustion catalysts that may present a fire hazard during a contact with combustible materials. Many hydrogen sensors are rather complicated, bulky devices and, in many cases, may require dedicated personnel to work with the equipment.

Among chemochromic type hydrogen detectors some of them are not stable in the environment and could crack, peel, or be washed off by rain. Existing hydrogen sensors have rather limited temperature endurance and cannot operate at high temperatures, for example, above 200° C., because of the potential damage to the system components, which limits their application areas.

Another disadvantage of the existing hydrogen sensors is that a hydrogen leak can be detected only as it is occurring, whereas in some practical systems it is important to know if a leakage has occurred at some point in the past. Lastly, most of the known hydrogen sensors are expensive because they involve costly equipment to produce and operate them or expensive materials to manufacture them, for example, high vacuum systems, fiber optic cables, palladium (Pd) films and the like.

U.S. Pat. No. 6,895,805 to Hoagland teaches a hydrogen gas indicator system having a multi-layered structure and comprising of the layers of hydrogen sensor material such as oxides of vanadium, yttrium, tungsten, molybdenum with the layer thickness of 0.2-10 microns, a catalyst material such as palladium (Pd), platinum (Pt), nickel (Ni), rhodium (Rh) with the layer thickness of 0.5-10 microns and a protective molecular diffusion barrier (e.g., Pd coating or a polymer film). The shortcoming of this invention is that it is rather difficult to manufacture the hydrogen sensor since it is multi-step process, which requires specialized expensive equipment, such as vacuum vapor deposition apparatus, sputtering, electrophoretic devices. Furthermore, the multi-layered structures are cumbersome to manufacture in a controlled manner.

Similarly, gasochromic hydrogen-sensing coating comprising the layers of $WO_3$ and Pt on a glass substrate was described by Witter et al. in *Solar Energy Materials and Solar Cells*, 84, 305, (2004). The $WO_3$ coating with the thickness of less that 1 micron is further coated with a film of Pt produced by sputtering technique. Exposing the coating to hydrogen resulted in its coloring; the process could be reversed by exposing the coating to air. This indicates that the system is reversible, which implies that hydrogen can be detected only when it is present.

Ping et al. in U.S. Patent Publication No. 2004/0023595 disclosed a thin-film hydrogen sensor consisting of Pd layer coated on the water-doped $WO_3$ layer coated on a substrate. The production of water-doped $WO_3$ films is accomplished by plasma-enhanced chemical vapor deposition method, which requires expensive special equipment. However the major problem with Pd-film coated films is that in the presence of high concentrations of hydrogen, palladium (Pd) hydride may be formed, which would adversely affect the stability of the film and the device, in general. Other shortcomings relate to the fact that the system works only in a reversible mode, and it may not work at temperatures above approximately 100° C., because water will evaporate from-doped $WO_3$ films.

Liu et al. in U.S. Patent Publication No. 2004/0037740 discloses a device for colorimetric hydrogen detection. It consists of a glass substrate, a vanadium oxide layer coated on the glass substrate and a palladium layer coated on the vanadium oxide layer. The disadvantage of the system is that the substrate is limited to a glass, which may significantly limit its application areas. Moreover, the device has a layered structure, which is difficult to manufacture in a controlled manner. Furthermore, the system operates in reversible mode only.

Mendoza et al in U.S. Pat. No. 6,535,658, describes a fiber optic system that employs a chemochromic indicator using layers of tungsten oxide and palladium. The procedure for making hydrogen-sensing material is complicated as it involves six steps. The device itself is also very complex since it includes a light source, an optical fiber, a glass rod and an optoelectronic detector. A similar concept is disclosed by Lee et al in U.S. Pat. No. 6,723,566. The inventors used a double layer gasochromic sensor structure comprising a glass substrate, tungsten-doped nickel oxide layer coated on the glass substrate and a palladium layer coated on the tungsten-nickel oxide layer. The system involves a complex optoelectronic system for monitoring hydrogen.

U.S. Pat. No. 5,849,073 to Sakamoto discloses a pigment for detecting hydrogen gas leakage comprising one of the platinum group metals and one of the compounds of aluminum, silicon, titanium, zinc, zirconium, tin, antimony and cerium. Since the compositions disclosed are typically quite impervious to gas penetration, the method requires very thin coatings, typically a thickness of 2 mils, with relatively high concentrations of active chemochromic compounds. The disadvantage of Sakamoto's formulations is that they are not specific to hydrogen.

Puri et al in U.S. Patent Publication 2004/0115818 teaches an apparatus for detecting a leak of fluid, such as hydrogen, from a vessel having inner and outer walls that includes a chemical material layer adjacent to the outer wall. The chemical material undergoes a chemical reaction with the fluid leaking through the outer wall producing a detectable odor or discoloration of the chemical material layer. The inventors propose to use ethanol solution of carotene in the presence of Raney nickel for detecting hydrogen by color change from yellow to colorless. This method, however, is rather complicated and may not be applicable for a variety of applications, such as detecting $H_2$ leak from joints, fittings, and the like.

Smith and Tracy describe a hydrogen sensor consisting of a hydrogen sensitive chemochromic coating, such as tungsten oxide, at the end of an optical fiber in a Preprint of Papers, *Amer. Chem. Soc., Div. Fuel Chem.*, 2004, 49, 968. A thin catalytic over-layer of palladium acts as a dissociation catalyst forming atomic hydrogen, which subsequently reacts with the $WO_3$. Pd layer coated by 300 nm thick coating of nano-phase titania. The shortcomings of this device are similar to those of multi-layered hydrogen sensors. Moreover, the system operates only in a reversible mode.

A gas-permeable chemochromic composition for hydrogen sensing is disclosed by Bokerman et al in U.S. Patent Publication 2007/0224081. The hydrogen sensor is based on a composition comprising a gas permeable matrix material encapsulating a chemochromic pigment that changes color in the presence of hydrogen. The encapsulating matrix materials are crosslinked polymers, preferably, silicone rubber or silicone resin. The chemochromic pigments are PdO and compounds of Mo and W supported on metal oxides, preferably, $TiO_2$ and $Al_2O_3$. The sensor has a layered structure consisting of at least two layers: a top layer comprising a pigment in a silicone matrix disposed on a clear silicone overcoat layer or a support that does not include pigment. Several shortcomings to the disclosed hydrogen sensor are as follows. The sensor is rather cumbersome to prepare since it requires a certain skill in producing a thin layer or a double-layer of the silicone matrix material. Furthermore, the disclosed hydrogen sensor requires a rather expensive material for manufacturing, a moisture curing silicone adhesive/sealant, which will increase the cost of the final product. Thirdly, due to the presence of a polymer matrix, which acts as a diffusion barrier for gases, the kinetics of color change is relatively slow. PdO-based pigment is not specific to hydrogen. Lastly, the presence of the polymer matrix significantly narrows the working temperature range of the hydrogen sensor from about minus 40° C. (below that temperature the polymer matrix hardens) to about plus 250° C. when it starts decomposing.

Thus, an improved low-cost, user-friendly and easy-to-prepare hydrogen detector with high detection specificity and sensitivity, resistance to chemical degradation, operable in a wide range of temperatures from minus 100° C. to plus 500° C., dependable and durable, stable and reproducible, with variable reversibility and inherently safe to operate in any environment is needed. The potential application areas for such a hydrogen detector include aerospace, transportation, hydrogen plants, oil refineries, ammonia plants, hydrogen reformers, fuel cell plants, chemical and analytical laboratories, and the like.

The present invention improves upon and overcomes many of the deficiencies of the prior art.

SUMMARY OF THE INVENTION

A primary objective of the present invention is to provide a method and composition for forming a durable and highly-sensitive, hydrogen-specific visual hydrogen detector for sensing a hydrogen leak or the presence of hydrogen in a confined environment in the wide range of hydrogen concentrations from approximately 0.1% to approximately 100% by volume.

A second objective of the present invention is to provide a visual hydrogen detector with variable reversibility, which means that it could easily alter the regeneration or bleaching time from seconds to days by a simple change in composition.

A third objective of the present invention is to provide a visual hydrogen detector that can operate in a wide range of temperatures from approximately minus 100° C. to approximately plus 500° C.

A fourth objective of the present invention is to provide a visual hydrogen detector that can selectively sense hydrogen in the presence of reducing and combustible gases such as hydrocarbons, carbon monoxide, ammonia, and the like.

A fifth objective of the present invention is to provide a visual hydrogen detecting composition that can be supported on a solid substrate, but preferably on porous, woven and fabric or paper substrates.

A sixth objective of the present invention is to provide a method and process for producing a visual hydrogen detector with variable reversibility.

A composition of matter for the visual detection of hydrogen gas includes a hydrogen sensitive pigment, a plurality of metal activator nanoparticles, and a porous substrate wherein the hydrogen sensitive pigment and the metal activator nanoparticles are attached thereto.

The hydrogen sensitive pigment is selected from at least one of oxides, hydroxides, hydrated oxides, acids, oxysalts and polyoxometalates of tungsten, molybdenum, vanadium, chromium and a combination thereof. More preferably, the hydrogen sensitive pigment is at least one of silico-tungstic acid (STA) $H_4[SiW_{12}O_{40}]$; phospho-tungstic acid (PTA) $H_3[P(W_3O_{10})_4]$); phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof.

The plurality of metal activator particles is a noble metal, such as, platinum, palladium, rhodium and iridium; most preferably, the noble metal is platinum.

The porous substrate is selected from at least one of a fibrous structure, a woven structure, and an open-cell structure; more preferably, the porous substrate is fabric, fiberglass tape, fiberglass cloth, glass fiber filter, filter paper, paper towel, synthetic paper, adhesive-backed fibrous materials, porous polymers and synthetic fiber fabric.

It is also preferred that the hydrogen sensitive pigment and the metal activator nanoparticles are attached to the porous substrate with the use of ultrasonic action.

A method for forming a visual detector of hydrogen gas includes a process of preparing a first aqueous mixture of a hydrogen sensitive pigment, preparing a second mixture of stable colloidal solution of metal activator nano-particles by adding a water-soluble protective polymer to an aqueous solution of a metal precursor and reducing the metal precursor with sodium borohydride, adding the stable colloidal solution of metal activator nano-particles of the second mixture to the first mixture of aqueous hydrogen sensitive pigment to form a third mixture, soaking a porous substrate in the third mixture comprising a stable colloidal solution of metal activator particles and aqueous mixture of hydrogen sensitive pigment removing the soaked porous substrate from the third mixture, and drying the porous substrate to form a visual hydrogen detector with reversible color change.

The method uses a hydrogen sensitive pigment selected from at least one of oxides, hydroxides, hydrated oxides, acids, oxysalts and polyoxometalates of tungsten, molybdenum, vanadium, chromium and a combination thereof; more preferably, the hydrogen sensitive pigment is silico-tungstic acid (STA) $H_4[SiW_{12}O_{40}]$; phospho-tungstic acid (PTA) $H_3[P(W_3O_{10})_4]$); phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof.

The plurality of metal activator particles is a noble metal such as, platinum, palladium, rhodium and iridium; more preferably, the noble metal is platinum.

The porous substrate is at least one of a fibrous structure, a woven structure, and an open-cell structure; more preferably, the porous substrate is fabric, fiberglass tape, fiberglass cloth, glass fiber filter, filter paper, paper towel, synthetic paper, adhesive-backed fibrous materials, porous polymers and synthetic fiber fabric.

It is also preferred that the method of producing a visual detector of hydrogen gas with reversible color change, further includes treating the porous substrate with the aqueous suspension of the hydrogen sensitive pigment and metal activator particles, then exposing the treated porous substrate to ultrasonic action to aid in penetrating the aqueous suspension of particles deep into the porous structure of the substrate material.

It is also preferred that the method of producing a visual detector of hydrogen gas with reversible color change, further includes the step of forming the hydrogen sensitive pigment in-situ on the surface of the porous substrate from a precursor compound by depositing the precursor compound on the porous substrate by soaking and drying and subsequently heating the support causing the formation of micron-sized hydrogen sensitive pigment particles that are strongly attached to the porous substrate.

The precursor compound is selected from at least one of ammonium meta-tungstate $[(NH_4)_6H_2W_{12}O_{40}.xH_2O]$ and ammonium molybdate $(NH_4)_2MoO_4$ or $(NH_4)_6 Mo_7O_{24}.4H_2O$.

A preferred hydrogen detector includes a hydrogen sensitive pigment selected from at least one of silico-tungstic acid (STA) $H_4[SiW_{12}O_{40}]$; phospho-tungstic acid (PTA) $H_3[P(W_3O_{10})_4]$); phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof, a plurality of metal activator nanoparticles selected from at least one of platinum, palladium, rhodium and iridium, and a porous substrate selected from the group consisting of fabric, fiberglass tape, fiberglass cloth, glass fiber filter, filter paper, paper towel, synthetic paper, adhesive-backed fibrous materials, porous polymers and synthetic fiber fabric, wherein the hydrogen sensitive pigment and the metal activator nanoparticles are attached thereto, forming a durable and highly-sensitive, hydrogen-specific visual hydrogen detector with variable reversibility, for sensing the presence of hydrogen in a confined environment in a wide range of hydrogen concentrations from approximately 0.1% to approximately 100% by volume and in a temperature range from approximately $-100°$ C. to approximately $500°$ C.

The hydrogen detector is preferably formed when the hydrogen sensitive pigment and the metal activator nanoparticles are attached to the porous substrate with the use of ultrasonic action.

Further objects and advantages of the present invention will be apparent from the following detailed description of a presently preferred embodiment which is illustrated schematically in the accompanying drawings.

DESCRIPTION OF THE PREFERRED EMBODIMENTS

Figure 1:
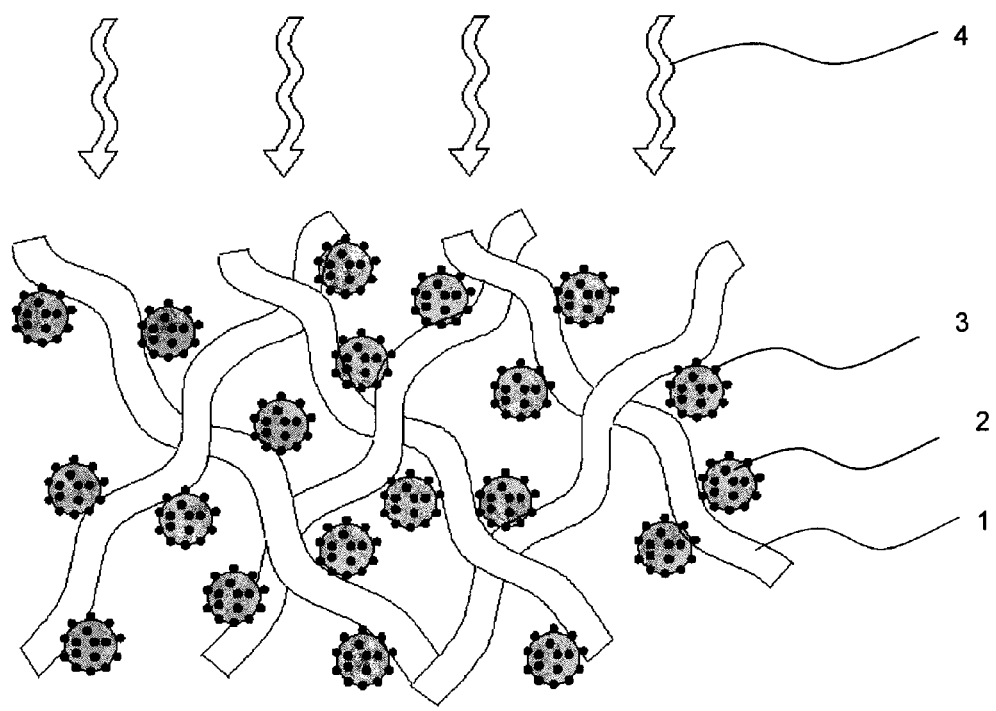
FIG. 1 is a sketch of a fibrous material such as a fabric or paper filter, with micro-particles of a hydrogen-sensing pigment doped with nano-sized metal activator particles.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

In general, the objectives stated above, can be accomplished by providing a composition comprising a hydrogen-sensitive pigment coated on a suitable substrate and doped with nano-sized metal activator particles. In the presence of hydrogen, the composition rapidly, in a matter of seconds, changes its color from white or light-grayish or light-tan to dark-gray or navy-blue or black depending on the exposure time and hydrogen concentration in the medium. After the cessation of the exposure to hydrogen gas, the original color of the composition is regenerated within a time span of seconds to hours to days as desired. Thus, depending on the particular application, the hydrogen detector of the present invention provides an opportunity to fine-tune the rate of regeneration or bleaching by changing the composition of the hydrogen sensing formulation.

The present invention is a chemical composition and a method for detecting a hydrogen leak from a variety of sources in a wide range of temperatures. The invention is also applicable for detecting and positively identifying hydrogen in a confined environment in a wide range of hydrogen concentrations. It improves upon a major shortcoming of the state-of-the-art hydrogen sensors, including chemochromic sensors, namely, complex multi-layered structures typically consisting of separate layers of a hydrogen sensor material, a catalyst material, a barrier, such as diffusion or protection, and a substrate. In some cases, the devices comprise up to six layers of materials, which makes manufacturing labor intensive and expensive. The hydrogen detector of the present invention does not require a layered structure. All components of the composition are mixed beforehand and then applied to a suitable substrate. The method of the invention does not involve or require any complex and expensive equipment or sophisticated electronic devices. The major requirements for the present invention are basic wet chemistry laboratory ware, such as beakers, stirrers, deionized water and the like.

The hydrogen detecting composition of the present invention consists of a hydrogen-sensitive pigment (HSP) combined with a metal activator or catalyst and the resulting composite is coated on a suitable substrate. The HSPs include oxides, hydroxides, hydrated oxides, acids, oxysalts and polyoxometalates of tungsten, molybdenum, vanadium, chromium or a combination thereof. The HSP is used in the form of an aqueous solution, or an aqueous suspension or slurry, depending on solubility of the HSP. Non-limiting examples of HSP are: silico-tungstic acid (STA) $H_4[SiW_{12}O_{40}]$; phospho-tungstic acid (PTA) $H_3[P(W_3O_{10})_4])$; phospho-molybdic acid (PMA) $H_3[P(Mo_3O_{10})_4]$; tungsten oxide ($WO_3$); tungstic acid ($H_2WO_4$); molybdic acid ($H_2MoO_4$); molybdenum oxide ($MoO_3$); chromium oxides and hydroxides, vanadium oxides and hydroxides. The HSP could be used in the hydrogen-detecting compositions as received, or could be formed in-situ on the surface of a porous substrate from a precursor compound. Non-limiting example of a precursor compound is ammonium meta-tungstate $[(NH_4)_6H_2W_{12}O_{40}\cdot xH_2O]$ that is deposited on a fibrous support by a simple soaking-and-drying technique, followed by heating of the support resulting in the formation of micron-sized tungsten oxide particles strongly attached to the fibers. Similarly, molybdenum oxide particles can be formed in-situ on the support from ammonium molybdate $[(NH_4)_2MoO_4$ or $(NH_4)_6MoO_{24}\cdot 4H_2O]$ as a precursor compound. A person skilled in the art can identify many related compounds which are deemed to be within the scope of the present invention.

The role of metal activators (MA) is to enhance the rates of coloration of the HSP upon exposure to hydrogen and regeneration or bleaching after the exposure is ceased. The metal activators include primarily noble and transition metals, including, but not limited to, platinum (Pt), palladium (Pd), iridium (Ir), rhodium (Rh), ruthenium (Ru), nickel (Ni), cobalt (Co). Platinum (Pt) is the preferred metal activator, added in small quantities to the hydrogen detector composition at the level of 0.001-5.0 wt. % (of HSP). The particle size diameter dimensions of MA are in the range from approximately 1 nanometer (nm) to approximately 100 nm, preferably, 1-10 nm. It is essential that the MA nano-particles exist in the form of a stable aqueous suspension; the suspension should be stable for at least a month. The stability of the aqueous MA suspension is enhanced by adding water-soluble protective polymers, such as polyvinylalcohol (PVA), polyvinylpryrollidone (PVP), and the like.

The role of a substrate is to support the HSP-MA composite and render the necessary mechanical properties to the complete hydrogen detecting system. Although the composite could be applied to any solid surface, the substrates with a porous or woven structure such as filter paper, glass fiber filters, fiberglass tape and cloth, fabric, synthetic paper, such as TYVEX® paper, and the like are preferable compared to solid smooth surfaces, because they provide high surface area and allow hydrogen gas to freely permeate through the system. (TYVEX is a registered trademark of the DuPont Company.)

In the present invention, the color change may be observed from both sides of the substrate. This is a significant advantage over the state-of-the-art sensors with the multi-layered impermeable structure. To increase the adherence of the composite to a substrate, water-soluble polymers such as PVP and the like could be added to the composite. In order to easily attach the hydrogen detector to the areas where hydrogen leak is expected, an adhesive-backed fibrous material, similar to a commercially available product, such as Band-Aid® adhesive strips, can be used as a support. (Band-Aid is a registered trademark of the Johnson & Johnson Company.)

The typical practice of this invention involves application of the aqueous solution of the HSP combined with MA nano-particles to a porous substrate such as a paper filter or the like. After the HSP/MA/substrate system is completely dry, typically, after leaving it undisturbed overnight, it is ready for detecting hydrogen. In case of a non-soluble HSP, such as tungstic acid, molybdenum and tungsten oxides, the suspensions of the HSP and MA are well mixed and applied to a substrate, followed by its drying. In order to improve the attachment of the HSP particles to a porous substrate, the inventor found it very useful to treat the substrate with the HSP-MA suspension under ultrasonicating conditions using a commonly used ultrasonic cleaner. The ultrasonic action results in disintegrating large particles into small ones and aids in penetrating the particles deep into the porous structure of the substrate material. The exposure of the HSP/MA/substrate composition to a stream of hydrogen gas or to any hydrogen-containing medium, results in a highly discernable color change from white, or light-grayish or light-tan to dark gray, navy-blue or black depending on the exposure time and hydrogen concentration in the medium.

One particular theory, which is not to be viewed as limiting to the present invention, is that the color change is due to two reactions: activation of molecular hydrogen over MA nano-particles and its dissociation into atomic hydrogen (reaction 1), and reduction of HSP by atomic hydrogen to its reduced (dark-colored) form (reaction 2):

$$H_2 \rightarrow 2H \text{ (catalyzed by MA nano-particles)} \quad (1)$$

$$M^{n+}=O+H \rightarrow M^{(n-1)+}-OH \quad (2)$$

where, H is hydrogen atom, $M^{n+}$ and $M^{(n-1)+}$ are oxidized and reduced forms of HSP, respectively. M is W, Mo, V, Cr.

When hydrogen flow is ceased, and the HSP/MA/substrate system is exposed to air, the reduced (dark-colored) form of the HSP is transformed (or oxidized) to its original light-colored form according to the following reaction:

$$M^{(n-1)+}-OH + \tfrac{1}{4}O_2 \rightarrow M^{n+}=O + \tfrac{1}{2}H_2O \qquad (3)$$

The rate of this bleaching reaction depends on the redox potential of the $M^{n+}/M^{(n-1)+}$ pair and can vary in a wide range, which explains the difference between rapidly- and slowly-regenerable HSP compositions. In particular, the change in the redox potential of the $M^{n+}/M^{(n-1)+}$ pair alters the rate of an electron transfer from the reduced form of HSP to oxygen and, thus, accelerates or slows down the bleaching process. In general, tungsten-based HSP feature faster bleaching kinetics compared to molybdenum-based HSP. Thus, tungsten-based HSP could be the basis for rapidly regenerable hydrogen detectors, and molybdenum-based HSP—for slowly-regenerable detectors. For example, STA-Pt and PTA-Pt compositions show fast kinetics for both coloration and bleaching reactions, whereas PMA-Pt rapidly acquires color, but bleaches very slowly (days). Furthermore, modifying polyoxometalates of W and Mo with hetero-atoms such as V, Co and the like, can alter its redox potential and accelerate or decelerate the rate of bleaching.

The present invention also discloses additional ways of controlling the bleaching kinetics of the hydrogen detector. It was found that addition of nano-sized particles of titania (TiO$_2$) to the hydrogen-sensing composition accelerates the kinetics of bleaching. The mechanism of the acceleration action of TiO$_2$ can be, most likely, attributed to its ability to photogenerate active oxidizing species such as hydroxyl radicals (OH.) that readily react with the reduced form of the HSP as follows:

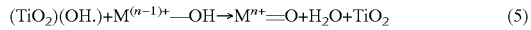

The preferred modification of TiO$_2$ is anatase.

On the other hand, if the objective is to slow down the kinetics of bleaching, some polymers could be added to the composition. The decelerating effect of polymers is attributed to creation of a diffusion barrier for oxygen molecules. The diffusion barrier retards the reaction (3), and thus, slows down the entire regeneration process. A number of polymers were tested and some of them showed the ability to prolong the bleaching process for several days and even weeks. Thus, the remarkable feature of the disclosed formulation is that by changing the composition of the HSP the time required for its complete regeneration could be varied or fine-tuned from a few seconds to several days. Since the original color of the HSP/MA/substrate composition is completely restored, it can be used repeatedly, which is an advantage over single-use irreversible chemochromic detectors based on Pd-containing pigments and the like.

The hydrogen detecting compositions of the present invention are highly specific to hydrogen, i.e., they do not show any color change in the presence of other reducing gases that are usually present in industrial sources of hydrogen such as carbon monoxide, methane, ethylene, acetylene, ammonia, etc. This can be explained by the fact that the MA particles do not activate reducing gases other than hydrogen, and, thus, do not transfer electrons from them to HSP. This is in contrast to some other existing hydrogen sensors that lack the specificity to hydrogen, for example, U.S. Pat. No. 5,849,073 to Sakamoto supra.

The components of the disclosed hydrogen detecting formulation are not prone to hydrogen-induced degradation, which allows for a wide working range of hydrogen concentrations in the tested gas from approximately 0.1% to approximately 100 v. %. The inorganic nature of both HSP and MA is conducive to a wide range of temperatures. The working temperature range depends on the type of the HSP used: the operation of polyoxometalate-based compositions is usually limited to about 150° C., whereas, metal oxide-type HSP can withstand temperatures up to 500° C. All types of HSP can operate at low range of temperatures, down to minus 50° C. and below. Pressure does not affect the performance of the hydrogen detecting compositions of the present invention.

Before going into experimental details of the invention, it would be useful to describe how color change in the hydrogen detecting compositions of the present invention is quantified. It is done by using a special spectrometric instrument calibrated and programmed with an algorithm specifically designed to quantify the color change using the following input parameters: L—lightness value, a—position on red-green axis value, and b—position on yellow-blue axis value. The combination of the above values results in the parameter ΔE as shown in Equation (4) below:

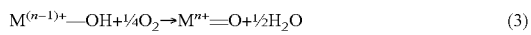

where, values L, a, b and L', a', b' relate to hydrogen detecting compositions after and before exposure to hydrogen, respectively. ΔE is proportional to the intensity of color change in the sample. Thus, the above equation gives a standard measurement, which enables quantifying and comparing color changes in the same or different samples. The greater the ΔE value, the greater the color change.

Reference is now made to FIG. 1, which shows that the hydrogen detecting composition of the present invention comprises a fibrous substrate 1 such as a paper filter, a fabric, or the like, and the micron-sized HSP particles 2 attached to the fibers, and nano-sized MA particles 3 deposited on the surface of the MA particles. Particular examples of HSP are tungsten oxide, tungstic acid, molybdenum oxide. Particular examples of MA are nano-particles of platinum, palladium, ruthenium and rhodium. Due to highly porous structure of the substrate the HSP/MA particles form a stable composite with the substrate. Upon exposure to the stream of hydrogen gas 4, the HSP/MA/substrate composition changes its color from light to dark.

Figure 2:
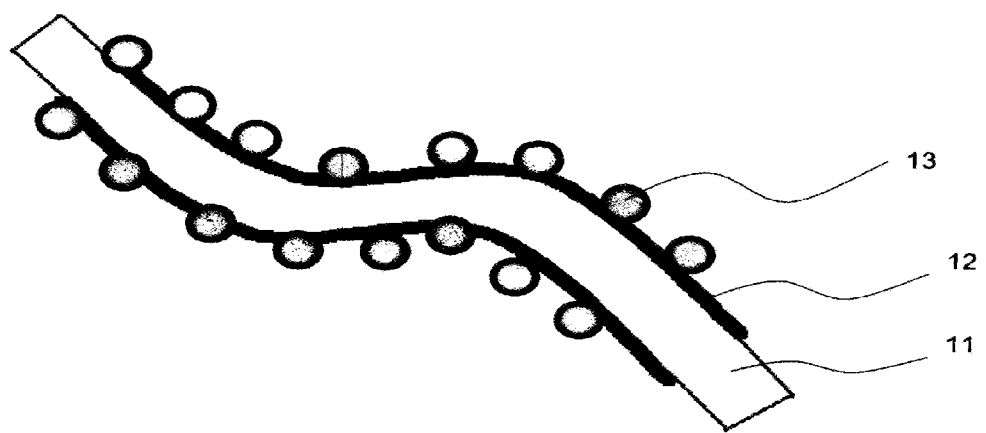
FIG. 2 shows a fragment of a fiber coated with a multi-molecular layer of polyoxometalate-based hydrogen-sensing pigment and nano-sized metal activator particles.

In FIG. 2, the hydrogen detecting composition of the present invention comprises a fibrous substrate 11 (only one fiber is shown) such as a filter paper, or a fabric, or the like, the MA nano-particles 13 attached to the fiber, and the multi-molecular layer of a water soluble HSP 12 covering the fibers and MA. In this embodiment, the particular examples of HSP are polyoxometalates of tungsten and molybdenum, such as STA, PTA, PMA and the like.

Figure 3:
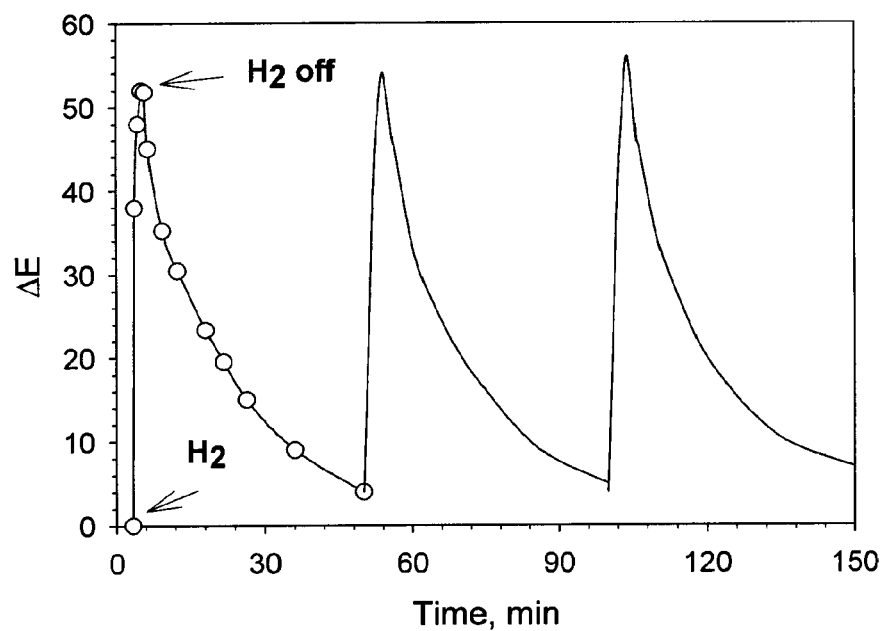
FIG. 3 is a graph depicting the kinetics of coloration and bleaching of the hydrogen detecting composition based on tungstic acid particles doped with Pt nano-particles on a paper filter wherein three cycles of coloration-bleaching occur within 150 minutes.

FIG. 3 is a graph depicting the kinetics of a color change of the hydrogen detecting formulation with a relatively fast (minutes) bleaching action based on Pt-doped tungstic acid supported on a paper filter. Beginning at time, τ=3 minutes hydrogen gas is turned on, within two or three minutes hydrogen detection occurs as shown by the coloration change scale (ΔE) and when the hydrogen gas is turned off, within approximately 50 minutes bleaching occurs and the hydrogen detecting formulation has almost returned to its original color, and two more coloration-bleaching cycles are plotted within a time frame of approximately 50 minutes per cycle.

Figure 4:
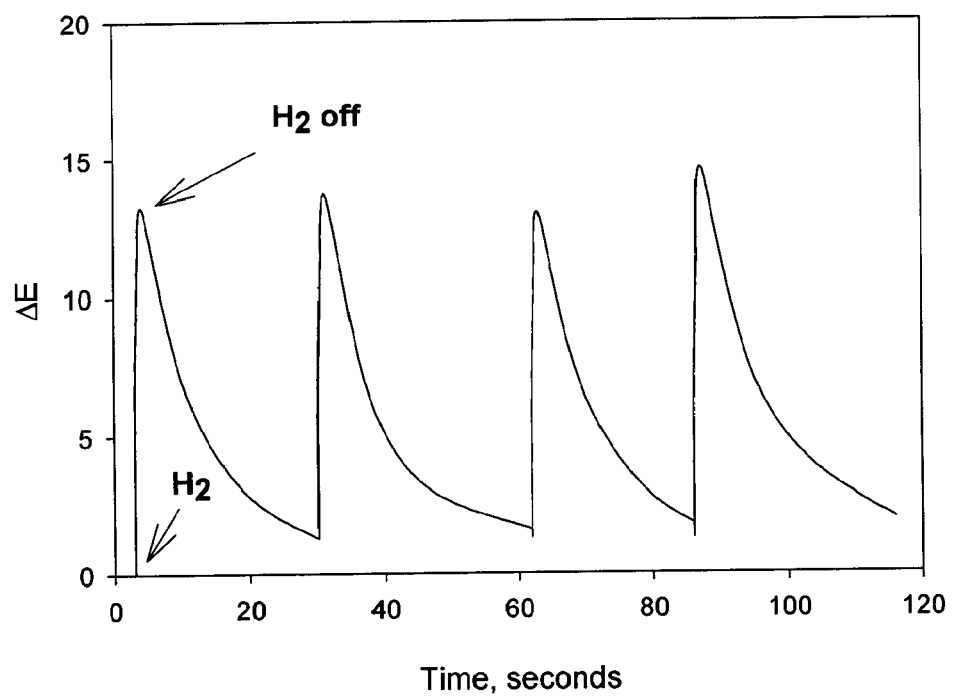
FIG. 4 is a graph showing the kinetics of a color change of the hydrogen detecting formulation with a very fast bleaching action showing four coloration-bleaching cycles within approximately 120 seconds. The composition is based on the combination of phospho-tungstic acid and Pt nanoparticles supported on a glass plate.

FIG. 4 is a graph showing the kinetics of a color change of the hydrogen detecting formulation with a very fast (seconds) bleaching action based on Pt-doped phospho-tungstic acid supported on a glass plate. Beginning at time, τ=3 seconds hydrogen gas is turned on, and within approximately two seconds hydrogen detection occurs as shown by the coloration change scale (ΔE). When the hydrogen gas is turned off, within approximately 30 seconds bleaching occurs and the hydrogen detecting formulation has almost returned to its original color, and three more coloration-bleaching cycles are plotted within a time frame of approximately 30 seconds per cycle.

Figure 5:
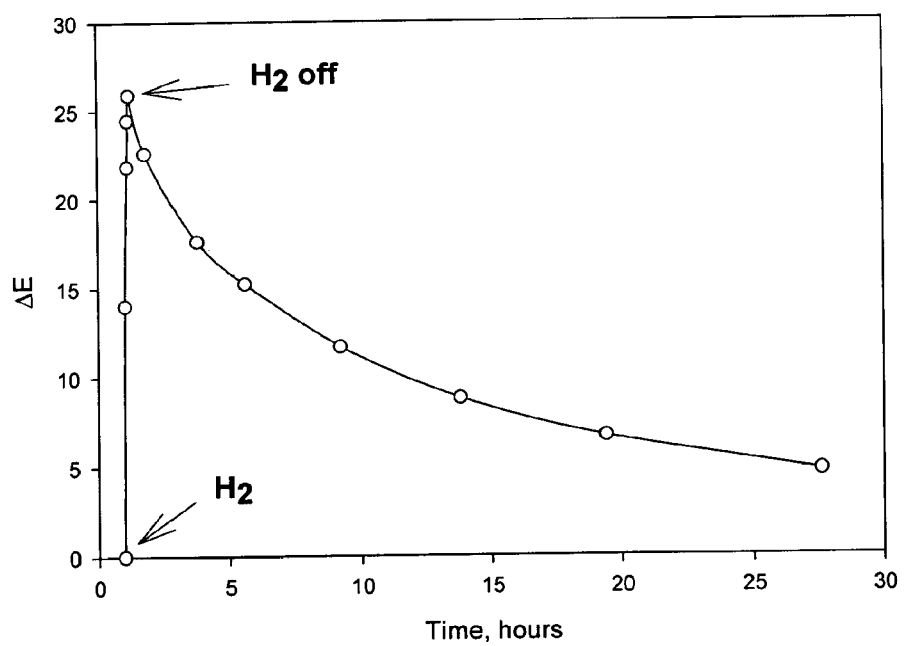
FIG. 5 is a graph depicting the kinetics of the color change of the hydrogen detecting formulation with a relatively slow bleaching action based on Pt-doped molybdenum oxide in-situ produced from ammonium molybdate supported on a glass filter wherein one coloration-bleaching cycle occurs in approximately 28 hours.

FIG. 5 is a graph depicting the kinetics of the color change of the hydrogen detecting formulation with a relatively slow (hours) bleaching action based on Pt-doped molybdenum oxide in-situ produced from ammonium molybdate supported on a glass filter. When hydrogen is turned on at time, τ=1 hour, within approximately 10 minutes hydrogen detection occurs as shown by the coloration change scale (ΔE). When the hydrogen gas is turned off, within approximately 28 hours bleaching occurs, and the hydrogen detecting formulation returns close to its original color.

Figure 6:
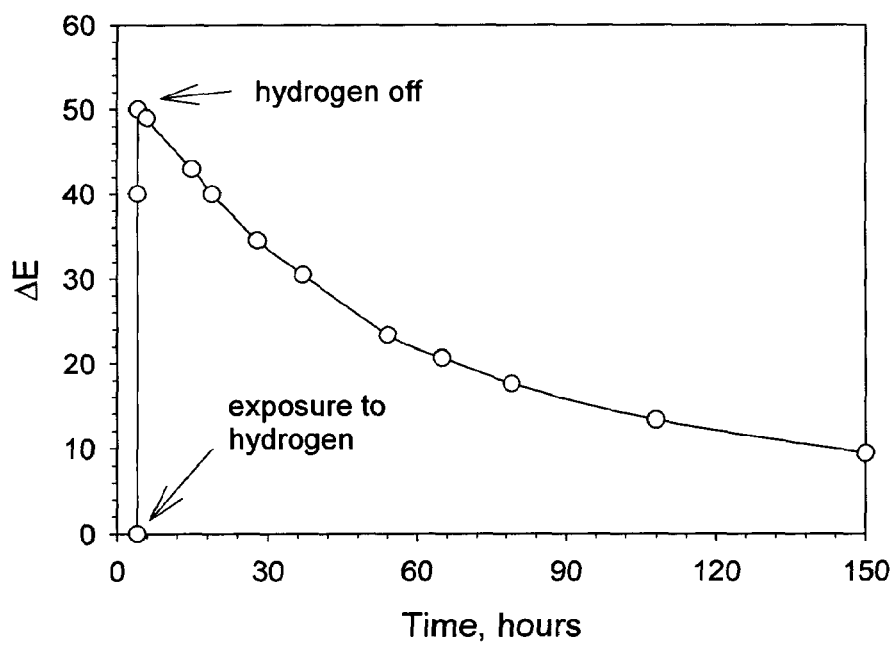
FIG. 6 is a graph showing the kinetics of the color change of the hydrogen detecting formulation with very slow bleaching action based on Pt-doped molybdenum oxide particles supported on a paper filter and treated with a polymer-based air diffusion barrier wherein one coloration-bleaching cycle occurs in approximately 150 hours.

FIG. 6 is a graph showing the kinetics of the color change of the hydrogen detecting formulation with very slow (days) bleaching action based on Pt-doped molybdenum oxide supported on a paper filter and treated with a polymer-based gas diffusion barrier. In FIG. 6, hydrogen is turned on at time, τ=4 hours, and within approximately 10-15 minutes hydrogen detection occurs as shown by the coloration change scale (ΔE). When the hydrogen gas is turned off, more than 150 hours are required for bleaching to occur, and the hydrogen detecting formulation gradually returns to its original color.

Thus, FIGS. 3-6 above, clearly demonstrate that changing the composition of the hydrogen-sensing formulations profoundly affects the reversibility of the hydrogen detector with the regeneration time varying in the range of a few seconds to several days.

Figure 7:
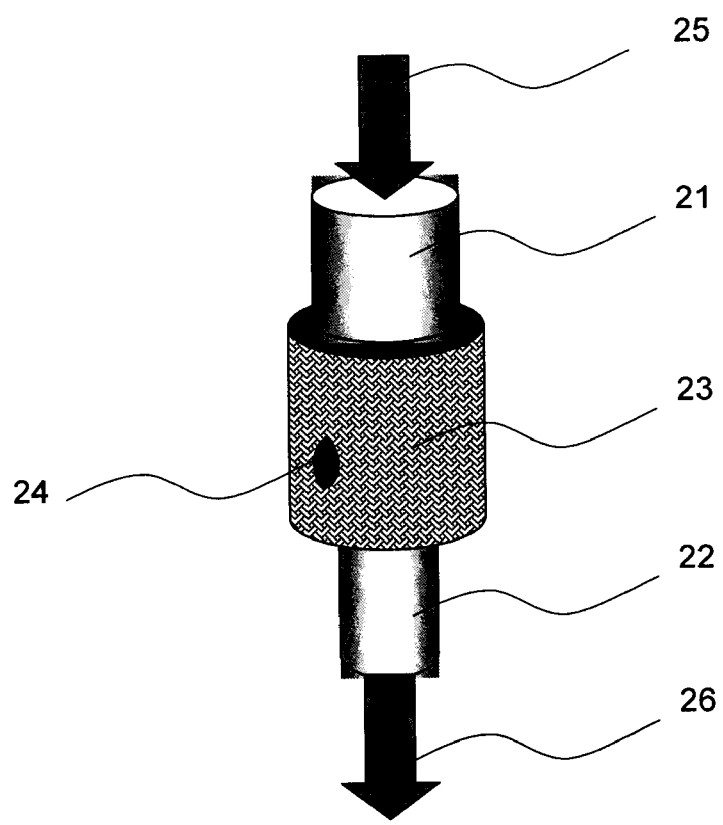
FIG. 7 shows a sketch of a heated joint between two tubings wrapped with a temperature-resistant glass fiber tape coated with the hydrogen-detecting composition. The dark spot on the tape shows the location of a hydrogen leak from the joint.

FIG. 7 shows a sketch of a heated joint between tubings 21 and 22 wrapped with a temperature-resistant fiberglass tape 23 coated with the hydrogen-detecting composition. The hot stream of hydrogen 25 under the pressure enters the tubing 21 and exits through the tubing 22 (shown as a stream 26). The dark spot 24 on the tape shows the location of a hydrogen leak from the joint. A woven structure and high-temperature (up to 500° C.) resistance of both the fiberglass tape 23 and the HSP/MA composite makes it suitable for the easy and convenient leak detection at very hot surfaces. The patent literature on the state-of-the-art hydrogen sensors shows no indication of comparable high-temperature resistance of the existing devices. The permeability of the disclosed hydrogen detector is a big advantage over known hydrogen sensors because it allows visual observation of color change on both sides of the detector, whereas existing multilayered sensors show color change only on one side of the device.

The present invention is illustrated with several Examples.

Example 1

Four aqueous solutions: A, B, C and D, were prepared as follows. Solution A: 5 g of silico-tungstic acid ($H_4[SiW_{12}O_{40}]$) were dissolved in 50 ml of deionized water. Solution B: 0.1 g of chloroplatinic acid ($H_2PtCl_6$) was dissolved in 50 ml of deionized water. Solution C, 1.0 g of polyvinylpyrrolidone $[(C_6H_9NO)_n]$ was dissolved in 20 ml of deionized water. Solution D: 0.2 g of sodium borohydride ($NaBH_4$) was dissolved in 50 ml of deionized water (Note that the solution D should be freshly prepared). 5 ml of the solution C was added to 40 ml of the solution B and the resulting solution (solution E) was carefully mixed. 5 ml of the solution D was added drop-wise (one drop every two-three seconds) to 45 ml of the solution E under well-stirred conditions (using a magnetic stirrer) at room temperature. During this procedure, the solution E noticeably darkened and some tiny bubbles of hydrogen could be observed. The stirring of the solution E continued until all hydrogen bubbles ceased to evolve. The resulting solution (solution F) represents a stable aqueous suspension containing platinum nano-particles with the dimensions of about 1 to 10 nm. Fifty (50) ml of solution A was carefully mixed with 20 ml of solution F producing solution G. A round-shape glass fiber filter with the diameter of 9 cm was soaked by solution G in a shallow glass container, pulled out of the solution and was left to dry overnight at room temperature. The resulting glass fiber filter was tested as a hydrogen detector. It showed fast kinetics of coloration (seconds) when exposed to a stream of hydrogen and fast kinetics of bleaching (minutes) when the hydrogen flow ceased.

Example 2

The procedure is similar to the Example 1, but phosphotunstic acid ($H_3[P(W_3O_{10})_4]$) was used instead of silico-tungstic acid, as a hydrogen sensitive pigment. The resulting detector showed fast kinetics of coloration (seconds) when exposed to a stream of hydrogen and bleaching (minutes) when the hydrogen flow ceased.

Example 3

The procedure is similar to the Example 1, but phosphomolybdic acid ($H_3[P(Mo_3O_{10})_4]$) was used instead of silico-tungstic acid, as a hydrogen sensitive pigment. The resulting hydrogen detector showed fast kinetics of coloration (seconds) when exposed to a stream of hydrogen, but very slow kinetics of bleaching (about 2 days).

Example 4

The procedure is similar to the Example 3, but 1 g of $TiO_2$ (modification: Degussa P25) with the particles size of 50 nm was added to the solution A. The kinetics of bleaching of the resulting hydrogen detector accelerated by factor 5 compared to one from the Example 3.

Example 5

Four (4) g of ammonium molybdate (AM) was dissolved in 100 ml of deionized water. A round-shape glass fiber filter with the diameter of 9 cm was soaked with the AM solution for 2 minutes in a shallow glass container, then pulled out of the solution and left to dry overnight at room temperature. The paper was placed in an electric furnace where it was heated to 280° C. for 3 hours. This was followed by soaking the glass filter in a stable aqueous suspension of Pt nano-particles (solution F, prepared in the Example 1). The paper was left to dry overnight at room temperature. The resulting paper featured fast kinetics of coloration (seconds) when exposed to hydrogen, and relatively slow rate of bleaching (hours).

Example 6

The procedure is similar to the Example 5, but ammonium meta-tungstate hydrate $[(NH_4)_6H_2W_{12}O_{40}\cdot xH_2O]$ was used instead of ammonium molybdate, and the heating temperature was 400° C., instead of 280° C. The resulting hydrogen detector featured fast kinetics of coloration (seconds) when exposed to hydrogen, and relatively fast rate of bleaching (minutes).

Example 7

A fiberglass tape with the dimensions of 5.1 by 10 cm and thickness of 1.5 mm was washed by acetone, dried in the air and heated in an electrical heater at 450° C. for 3 hours to remove an organic binder. It was cooled to room temperature and soaked with the aqueous solution of AM prepared in the Example 5. It was dried overnight and then heated in an electrical oven at 300° C. for 3 hours. The tape was cooled to room temperature and soaked with the solution F prepared in the Example 1. The tape was left to dry overnight at room temperature. The resulting hydrogen detector showed fast kinetics of coloration (seconds) when exposed to hydrogen and relatively slow kinetics of bleaching (several hours). The hydrogen detector performed at temperatures as high as 500° C. At high temperatures (about 100° C.), the kinetics of both coloration and bleaching were fast (seconds and minutes, respectively).

Example 8

Two (2) g of tungstic acid ($H_2WO_4$) was suspended in 50 ml of deionized water, and under well-stirred condition was mixed with 20 ml of the solution F prepared in the Example 1. A paper filter with the diameter of 7 cm was placed in the beaker with the resulting suspension, and the beaker was placed inside a ultra-sonicator. The suspension with the paper filter in it was sonicated for 0.5 hour, and the paper was removed from the beaker and left to dry overnight at room temperature. The resulting hydrogen detector showed both high rates of coloration (seconds) and bleaching (minutes).

Example 9

The procedure is similar to the Example 8, but molybdenum oxide ($MoO_3$) was used instead of tungstic acid. The hydrogen detector showed fast kinetics of coloration (seconds), but slow rate of bleaching (2 days).

In summary, there are several application areas for the visual hydrogen detector of the present invention. First, hydrogen leak detection, wherein the detector is used to determine the location of a hydrogen leak source. Second, hydrogen gas detection, such as, in determining if hydrogen is present in any gas stream or any confined environment, such as, a room, a car cabin, a space shuttle cabin, and the like. Third, hydrogen gas identification, since the detector is highly selective toward hydrogen, it can determine if the tested gas entirely or partially consists of hydrogen. Fourth, hydrogen gas quantification, wherein the detector can determine approximate content of hydrogen in a mixture with other gases.

The developed visual hydrogen sensors can be used to increase the safety level at nuclear power stations, hydrogen tanks, cryogenic storage systems, hydrogen plants, hydrocarbon reformers, fuel cell-based power sources, hydrogen-fueled vehicles and other areas where hydrogen is produced, stored and utilized.

For the first time, a process and composition is provided that produces a commercially viable, user-friendly, easy-to-prepare, durable, highly sensitive, hydrogen-specific visual hydrogen detector with variable or tunable reversibility. The reversibility of the hydrogen detector occurs at a controlled rate of time from a few seconds to several days, such that when the original color of the hydrogen-sensitive pigment is restored, the visual hydrogen detector can be used repeatedly. The hydrogen detector of the present invention does not show any color change in the presence of other reducing gases that are usually present in industrial sources of hydrogen such as carbon monoxide, methane, ethylene, ammonia and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of forming a variable or tunable visual detector for hydrogen, comprising the steps of:
    selecting a hydrogen sensitive pigment from oxides, hydroxides, hydrated oxides, acids, oxysalts and polymetalates of tungsten, molybdenum, vanadium, chromium, and a combination, thereof;
    selecting a plurality of noble metal nanoparticles from at least one of platinum, palladium, rhodium and iridium;
    selecting a nonlayered substrate selected from one of a fibrous and woven structure; and
    combining the hydrogen sensitive pigment and the plurality of nanoparticles to the substrate; and
    forming a variable or tunable visual detector by penetrating the substrate with the hydrogen sensitive pigment and the nanoparticles using an ultrasonic signal to penetrate the substrate with the hydrogen sensitive pigment and the nanoparticles.

2. The method of claim 1, wherein the hydrogen sensitive pigment is selected from at least one of silico-tungstic acid (STA) $H_4[SiW_{12}O_{40}]$; phospho-tungstic acid (PTA) $H_3[P(W_3O_{10})_4]$; phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof.

3. The method of claim 1, wherein the noble metal is platinum.

4. The method of claim 1, wherein the substrate is selected from the group consisting of fabric, fiberglass tape, fiberglass cloth, glass fiber filter, filter paper, paper towel, synthetic paper, adhesive-backed fibrous materials and synthetic fiber fabric.

5. The method of claim 3, wherein the hydrogen sensitive pigment selected from at least one of silico-tungstic acid (STA) $H_4[SiW_{12}O_{40}]$; phospho-tungstic acid (PTA) $H_3[P(W_3O_{10})_4]$; phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof, and includes the step of:
    adding the plurality of platinum metal activator nanoparticles to the hydrogen detector at a level of approximately 0.0001 to approximately 5.0 weight percent of the hydrogen sensitive pigment, wherein the nonlayered substrate is selected from the group consisting of fabric, fiberglass tape, fiberglass cloth, glass fiber filter, filter paper, paper towel, synthetic paper, adhesive-backed fibrous materials and synthetic fiber fabric, wherein the hydrogen sensitive pigment and the metal activator nanoparticles penetrate the substrate material, forming a durable and highly-sensitive, hydrogen-specific visual hydrogen detector with variable reversibility, that detects the presence of hydrogen in a confined environment in a wide range of hydrogen concentrations from approximately 0.1% to approximately 100% by volume and in a temperature range from approximately −100° C. to approximately 500° C., and the tungsten based hydrogen sensitive pigment has a coloration-bleaching cycle wherein coloration in the presence of hydrogen occurs in approximately 2 to approximately 3 minutes and the bleaching cycle in the absence of hydrogen occurs in approximately 50 minutes.

6. The method of claim 1, wherein the hydrogen sensitive pigment is selected from a molybdenum based hydrogen sensitive pigment selected from a molybdenum based hydrogen sensitive pigment, the plurality of metal activator nanoparticles is selected from molybdenum based hydrogen sensitive pigment, the plurality of metal activator nanoparticles is selected from at least one of platinum, palladium, rhodium and iridium added to the hydrogen detector at a level of approximately 0.0001 to approximately 5.0 weight percent of the hydrogen sensitive pigment, the non-layered porous substrate is selected from the group consisting of fabric, fiberglass tape, fiberglass cloth, glass fiber filter, filter paper, paper towel, synthetic paper, adhesive-backed fibrous materials, and synthetic fiber fabric, wherein the hydrogen sensitive pigment and the metal activator nanoparticles penetrate the substrate material forming a durable and sensitive, hydrogen-specific visual hydrogen detector with variable reversibility, that detects the presence of hydrogen in a confined environment in a wide range of hydrogen concentrations from approximately 0.1% to approximately 100% by volume and in a temperature range from approximately −100 C. to approximately 500 C. and the molybdenum based hydrogen sensitive pigment has a coloration-bleaching cycle wherein coloration in the presence of hydrogen occurs in approximately 2 to approximately 3 seconds and the bleaching cycle in the absence of hydrogen occurs in approximately two days.

7. The method of claim 1, wherein the hydrogen sensitive pigment is tungstic acid particles doped with platinum nanoparticles on a paper filter substrate wherein one coloration-bleaching cycle occurs within approximately 50 minutes.

8. The method of claim 1, further comprising the steps of:
selecting a hetero-atom from at least one of vanadium and cobalt; and
changing the rate of bleaching in the absence of hydrogen with the hetero-atom.

9. A method of forming a variable or tunable visual detector for hydrogen, comprising the steps of:
selecting a hydrogen sensitive pigment;
selecting a plurality of noble metal nanoparticles;
selecting a nonlayered substrate; and
combining the hydrogen sensitive pigment and the plurality of nanoparticles to the substrate; and
forming a variable or tunable visual detector by using an ultrasonic signal to penetrate the substrate with the hydrogen sensitive pigment and the nanoparticles.

10. The method of claim 9, wherein the step of selecting the hydrogen sensitive pigment includes the step of:
selecting the hydrogen sensitive pigment from oxides, hydroxides, hydrated oxides, acids, oxysalts and polymetalates of tungsten, molybdenum, vanadium, chromium, and a combination, thereof.

11. The method of claim 9, wherein the step of selecting a plurality of noble metal nanoparticles includes the step of:
selecting the plurality of noble metal nanoparticles from at least one of platinum, palladium, rhodium and iridium.

12. The method of claim 9, wherein the step of selecting a nonlayered substrate includes the step of:
selecting a nonlayered substrate from one of a fibrous and woven structure.

13. The method of claim 9, wherein the steps of selecting the hydrogen sensitive pigment and selecting a plurality of noble metal nanoparticles includes the steps of:
selecting the hydrogen sensitive pigment from oxides, hydroxides, hydrated oxides, acids, oxysalts and polymetalates of tungsten, molybdenum, vanadium, chromium, and a combination, thereof,
selecting the plurality of noble metal nanoparticles from at least one of platinum, palladium, rhodium and iridium.

14. The method of claim 9, wherein the hydrogen sensitive pigment is selected from at least one of silico-tungstic acid (STA) $H_4[SiW_{12}O_{40}]$; phospho-tungstic acid (PTA) $H_3[P(W_3O_{10})_4]$); phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof.

15. The method of claim 9, wherein the hydrogen sensitive pigment selected from at least one of silico-tungstic acid (STA) $H_4[SiW_{12}O_{40}]$; phospho-tungstic acid (PTA) $H_3[P(W_3O_{10})_4]$); phospho-molybdic acid (PMA) $H_3[P(Mo_3O_{10})_4]$; tungsten oxide ($WO_3$); tungstic acid ($H_2WO_4$); molybdenum oxide ($MoO_3$) and a combination thereof, and includes the step of:
adding the plurality of platinum metal activator nanoparticles to the hydrogen detector at a level of approximately 0.0001 to approximately 5.0 weight percent of the hydrogen sensitive pigment, wherein the nonlayered substrate is selected from the group consisting of fabric, fiberglass tape, fiberglass cloth, glass fiber filter, filter paper, paper towel, synthetic paper, adhesive-backed fibrous materials and synthetic fiber fabric, wherein the hydrogen sensitive pigment and the metal activator nanoparticles penetrate the substrate material, forming a durable and highly-sensitive, hydrogen-specific visual hydrogen detector with variable reversibility, that detects the presence of hydrogen in a confined environment in a wide range of hydrogen concentrations from approximately 0.1% to approximately 100% by volume and in a temperature range from approximately −100° C. to approximately 500° C., and the tungsten based hydrogen sensitive pigment has a coloration-bleaching cycle wherein coloration in the presence of hydrogen occurs in approximately 2 to approximately 3 minutes and the bleaching cycle in the absence of hydrogen occurs in approximately 50 minutes.

16. The method of claim 9, wherein the hydrogen sensitive pigment is selected from a molybdenum based hydrogen sensitive pigment selected from a molybdenum based hydrogen sensitive pigment, the plurality of metal activator nanoparticles is selected from molybdenum based hydrogen sensitive pigment, the plurality of metal activator nanoparticles is selected from at least one of platinum, palladium, rhodium and iridium added to the hydrogen detector at a level of approximately 0.0001 to approximately 5.0 weight percent of the hydrogen sensitive pigment, the non-layered porous substrate is selected from the group consisting of fabric, fiberglass tape, fiberglass cloth, glass fiber filter, filter paper, paper towel, synthetic paper, adhesive-backed fibrous materials, and synthetic fiber fabric, wherein the hydrogen sensitive pigment and the metal activator nanoparticles penetrate the substrate material forming a durable and sensitive, hydrogen-specific visual hydrogen detector with variable reversibility, that detects the presence of hydrogen in a confined environment in a wide range of hydrogen concentrations from approximately 0.1% to approximately 100% by volume and in a temperature range from approximately −100 C. to approximately 500 C. and the molybdenum based hydrogen sensitive pigment has a coloration-bleaching cycle wherein coloration in the presence of hydrogen occurs in approximately 2 to approximately 3 seconds and the bleaching cycle in the absence of hydrogen occurs in approximately two days.

17. The method of claim 9, wherein the hydrogen sensitive pigment is tungstic acid particles doped with platinum nanoparticles on a paper filter substrate wherein one coloration-bleaching cycle occurs within approximately 50 minutes.

\* \* \* \* \*